United States Patent [19]

Steiner et al.

[11] Patent Number: 4,937,387
[45] Date of Patent: Jun. 26, 1990

[54] PROCESSES FOR PREPARING DIARYL SULFONES

[75] Inventors: Ulrich A. Steiner, North Plainfield; Walter T. Reichle, Warren, both of N.J.

[73] Assignee: Amoco Corporation, Chicago, Ill.

[21] Appl. No.: 235,357

[22] Filed: Aug. 23, 1988

Related U.S. Application Data

[63] Continuation-in-part of Ser. No. 904,009, Sep. 5, 1986, abandoned.

[51] Int. Cl.$^5$ ........................................... C07C 147/06
[52] U.S. Cl. ..................................................... 568/34
[58] Field of Search ...................... 568/34; 260/505 P; 562/83

[56] References Cited

U.S. PATENT DOCUMENTS

| | | | |
|---|---|---|---|
| 2,470,896 | 5/1949 | Mavity | 260/505 P |
| 2,556,429 | 6/1951 | Lee | 568/34 |
| 2,593,001 | 4/1952 | Bender et al. | 568/34 |
| 3,701,806 | 10/1972 | Keogh | 568/34 |
| 3,935,237 | 1/1976 | Davidsohn | 250/505 S |
| 3,946,037 | 3/1976 | Koebner | 260/505 E |
| 4,172,852 | 10/1979 | Ark et al. | 568/34 |

FOREIGN PATENT DOCUMENTS 1572916  8/1980  United Kingdom .

Primary Examiner—Mary E. Ceperley
Attorney, Agent, or Firm—William H. Magidson; Ralph C. Medhurst

[57] ABSTRACT

An improvement in processes for preparing diaryl sulfones comprising adding a limited amount of water to the reaction product mixture of such processes to form a heavier aqueous phase containing unreacted monosubstituted benzene sulfonic acid with less than an equal amount of water, separating the aqueous phase, and dehydrating the aqueous phase to recover the unreacted sulfonic acid for forming additional diaryl sulfone.

9 Claims, No Drawings

PROCESSES FOR PREPARING DIARYL SULFONES

FIELD OF THE INVENTION

This application is a continuation-in-part of application Ser. No. 904,009, filed Sept. 5, 1986, now abandoned. This invention relates to an improvement in processes for preparing diaryl sulfones and, in particular, to an improved process for preparing 4,4'-dichlorodiphenyl sulfone.

BACKGROUND OF THE INVENTION

It is known that diaryl sulfones can be synthesized by contacting a monosubstituted benzene with a monosubstituted benzene sulfonic acid at elevated temperatures. Also known is that such syntheses generally achieve only partial conversion of the sulfonic acid with the unreacted sulfonic acid being discarded in the recovery of the desired diaryl sulfone product.

For example, in U.S. Pat. No. 2,593,001 to Bender et al., there is described a synthesis method involving the counter-current reaction of monoclorobenzene vapor with benzene sulfonic acid to form p-monochlorodiphenyl sulfone. Though the proposed method is described to be of good yield, the resulting product mixture contains nearly as much unreacted sulfonic acid as diaryl sulfone product.

To recover the diaryl sulfone, Bender teaches washing away the unreacted sulfonic acid with copious amounts of water. This separation method is conventional in industrial practices. Even in processes where sulfonic acid is the principal and desired product, such as the processes described in U.S. Pat. Nos. 3,935,237 and 3,946,037, large amounts of water, generally well in excess of the amount of benzene sulfonic acid produced, are employed to separate the benzene sulfonic acid as an aqueous solution from the diaryl sulfone. However, in using such large amounts of water, the sulfonic acid is rendered practically useless for forming additional diaryl sulfone.

It is essential in forming diaryl sulfones that the reaction medium be maintained substantially anhydrous during the reaction. While amounts of water up to about one percent can be tolerated, amounts of water substantially greater than this are desirably avoided as the presence of water leads to very low reaction rates. Consequently, the aqueous solution of sulfonic acid from the conventional diaryl sulfone recovery cannot be recycled to form additional product due to its large water content.

Further, dehydration of the aqueous sulfonic acid has been economically prohibitive due to the large amounts of water used to recover the desired diaryl sulfone product. Therefore, unreacted sulfonic acid, heretofore, has been treated, as it was described in Bender, as by-product waste.

Present commercial synthesis of diaryl sulfones generally produces sulfonic acid then "captures" it by forming a sulfonyl chloride derivative by reacting thionyl chloride with the sulfonic acid, either as it is produced (e.g. U.S. Pat. Nos. 3,701,806 and 4,172,852) or subsequent to its production (e.g. U.K. Patent No. 1,572,916). The aromatic sulfonyl chloride then is reacted with a monosubstituted benzene in the presence of ferric chloride catalyst to yield the desired diaryl sulfone. These methods of producing diaryl sulfone are sufficiently advantageous and efficient for commercial operations. However, thionyl chloride is a relatively expensive chemical which is lost in the process as sulfur dioxide and hydrochloric acid off-gases.

SUMMARY OF THE INVENTION

The present invention relates to an improvement in processes for preparing diaryl sulfones which processes comprise contacting a monosubstituted benzene having the formula:

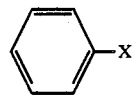

wherein X is hydrogen, halogen, a saturated alkyl radical having from 1 to 4 carbon atoms, or mixtures thereof, with a monosubstituted benzene sulfonic acid having the formula:

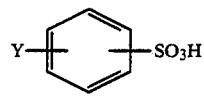

wherein Y is hydrogen, halogen, a saturated alkyl radical having from 1 to 4 carbon atoms, or mixtures thereof; thereby forming a reaction product mixture comprising at least one diaryl sulfone and unreacted monosubstituted benzene sulfonic acid.

The improvement of this invention comprises the steps of:

(a) adding a limited amount of water to the reaction product mixture thereby forming in the reaction product mixture a heavier aqueous phase containing unreacted monosubstituted benzene sulfonic acid with a less than equal amount of water and a lighter organic phase containing diaryl sulfone;

(b) separating the aqueous phase from the lighter organic phase;

(c) dehydrating the aqueous phase thereby recovering unreacted substantially anhydrous monosubstituted benzene sulfonic acid; and (d) contacting the recovered unreacted monosubstituted benzene sulfonic acid with a monosubstituted benzene thereby forming additional diaryl sulfone.

As the improvement of this invention recovers unreacted monosubstituted benzene sulfonic acid with minimal amounts of water, the aqueous sulfonic acid can be dehydrated readily enabling its use as a reactant to form additional diaryl sulfone. The recovery and further conversion of the sulfonic acid by this invention is a simple and efficient method to greatly increase the yield of diaryl sulfones.

The production of 4,4'-dichlorodiphenyl sulfone is particularly enhanced by employing the improvement of this invention together with a continuous or semicontinuous counter-current contacting of liquid p-chlorobenzene sulfonic acid with monochlorobenzene vapor to form 4,'-dichlorodiphenyl sulfone.

Accordingly, in one aspect, this invention provides an improved process for preparing 4,4'-dichlorodiphenyl sulfone which process comprises:

(a) passing liquid p-chlorobenzene sulfonic acid into a reaction zone while passing monochlorobenzene vapor into the reaction zone counter-current to the p-chlorobenzene sulfonic acid thereby forming 4,4'-dichlorodiphenyl sulfone;

(b) removing unreacted p-chlorobenzene sulfonic acid with 4,4'-dichlorodiphenyl sulfone from the reaction zone as a reaction product mixture;

(c) adding a limited amount of water to the reaction product mixture thereby forming in the reaction product mixture a heavier aqueous phase containing unreacted p-chlorobenzene sulfonic acid with a less than equal amount of water, and a lighter organic phase containing 4,4'-dichlorodiphenyl sulfone;

(d) separating the aqueous phase from the lighter organic phase;

(e) dehydrating the aqueous phase thereby recovering unreacted substantially anhydrous p-chlorobenzene sulfonic acid;

(f) repeating step (a) with the recovered p-chlorobenzene sulfonic acid; and (g) recovering 4,4'-dichlorodiphenyl sulfone.

In this improved process, p-chlorobenzene sulfonic acid is partially converted in a counter-current reaction system with monochlorobenzene to form 4,4'-dichlorodiphenyl sulfone. The unconverted sulfonic acid is separated from the crude sulfone product with a minor amount of water and the aqueous acid is dehydrated and then returned to the reaction zone to form additional 4,4'-dichlorodiphenyl sulfone.

In another aspect, this invention comprises a process for preparing 4,4'-dichlorodiphenyl sulfone which comprises the steps of:

(a) reacting liquid p-chlorobenzene sulfonic acid in a reaction zone with monochlorobenzene thereby forming 4,4'-dichlorodiphenyl sulfone;

(b) removing unreacted p-chlorobenzene sulfonic acid with 4,4'-dichlorodiphenyl sulfone from the reaction zone as a reaction product mixture;

(c) reacting a sulfonating agent comprising sulfur trioxide with an excess of monochlorobenzene thereby forming predominately p-chlorobenzene sulfonic acid product mixture with monochlorobenzene entrainer;

(d) combining 4,4'-dichlorodiphenyl sulfone formed in step (b) and p-chlorobenzene sulfonic acid product mixture formed in step (c);

(e) forming an aqueous composition comprising the composition of step (d) wherein the weight ratio of chlorobenzene sulfonic acid to water in the composition is about 1:1 to 4:1 thereby forming a heavier aqueous phase containing p-chlorobenzene sulfonic acid and a lighter organic phase containing 4,4'-dichlorodiphenyl sulfone;

(f) separating the aqueous phase from the lighter organic phase;

(g) dehydrating the aqueous phase thereby recovering unreacted substantially anhydrous chlorobenzene sulfonic acid; and (h) contacting the recovered unreacted chlorobenzene sulfonic acid with monochlorobenzene thereby forming additional 4,4'-dichlorodiphenyl sulfone.

DETAILED DESCRIPTION OF THE INVENTION

It has been found that processes for making diaryl sulfones from monosubstituted benzenes and monosubstituted benzene sulfonic acids are made significantly more efficient by incorporating the process improvements according to the present invention. The process improvements involve recovering unreacted sulfonic acid from the process and then recycling the recovered acid back to the process for further conversion to diaryl sulfone.

More particularly, the process improvements of the present invention involve the following steps. First, a heavier aqueous phase which contains unreacted sulfonic acid and a lighter organic phase containing diaryl sulfone is formed in the reaction product mixture from the diaryl sulfone synthesis. The aqueous phase is separated from the organic phase and then dehydrated to recover the sulfonic acid. Next, the recovered sulfonic acid is recycled to produce additional diaryl sulfone. Advantageously, a monoaryl sulfonic acid precursor for the diaryl sulfone is formed by sulfonating the aromatic compound and adding same to the product diaryl sulfone before adding water to the product diaryl sulfone. In this way it is possible to produce both the monoaryl sulfonic acid and diaryl sulfone using one purification system instead of two.

In general, the process improvement of the present invention is applicable to any process in which a substituted sulfonic acid is not fully consumed in the formation of diaryl sulfones. Such processes involve contacting a monosubstituted benzene with a monosubstituted benzene sulfonic acid to form at least one diaryl sulfone. The processes may be batch processes, such as mixing the two aromatic compounds together or sparging monosubstitutedd benzene through liquid monosubstituted benzene sulfonic acid, or continuous or semi-continuous processes such as the counter-current reaction of monosubstituted benzene vapor with liquid monosubstituted benzene sulfonic acid. These processes are described, for example, in U.S. Pat. No. 2,593,001, which disclosure is incorporated herein by reference, or are otherwise known in the art, and therefore are not elaborated herein.

One particular process for which the improvement of the present invention is especially applicable is the continuous or semi-continuous process for forming 4,4'-dichlorodiphenyl sulfone described in general in U.S. Pat. No. 2,593,001 to Bender et al., which disclosure is incorporated herein by reference. This improved process involves passing liquid p-chlorobenzene sulfonic acid into a reaction zone in which monochlorobenzene vapor is passed counter-currently. In the reaction zone, 4,4'-dichlorodiphenyl sulfone forms by way of a heterogeneous reaction which may be overall represented by the following equation:

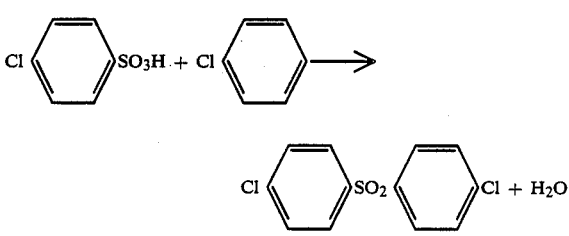

A mixture of dichlorodiphenyl sulfone isomers is formed with the desired 4,4'-isomer being preponderant (generally, >87%). The liquid reaction product mixture also comprises unreacted chlorobenzene sulfonic acid and monochlorobenzene as well as water and various by-products and impurities.

According to the improvement of the present invention, a lower aqueous phase containing unreacted chlorobenzene sulfonic acid and an upper phase containing 4,4'-dichlorodiphenyl sulfone is formed in the reaction product mixture after adding a limited amount of water. The aqueous phase is separated from the organic phase and then dehydrated to recover chlorobenzene sulfonic acid. This recovered sulfonic acid is then returned as liquid to the reaction zone to be further converted to 4,4'-dichlorodiphenyl sulfone. The 4,4'-dichlorodiphenyl sulfone is recovered by conventional means as the process is continuous or semi-continuous.

The improved process of forming 4,4'-dichlorodiphenyl sulfone results in maximum conversion of chlorobenzene sulfonic acid by recovering, dehydrating and recycling unreacted acid. In addition, the improved process minimizes formation of undesired sulfone isomers and other by-products.

In conventional processes, where unreacted chlorobenzene sulfonic acid is not recyclable, maximum conversion of the sulfonic acid in its pass through the reaction zone is a primary interest. To increase conversion, long retention times and high reaction temperatures are employed. However, these conditions also lead to formation of large percentages of undesirable sulfone isomers and other by-products.

Due to the improvement of this invention, maximizing the conversion of the reactants in a single pass through the reaction zone is not of primary concern as unreacted chlorobenzene sulfonic acid is recovered, dehydrated and recycled for further conversion. Accordingly, the present invention allows the employment of more moderate reaction conditions which provide efficient conversion with minimal formation of undesired isomers and other by-products.

In the present improved process of forming 4,4'-dichlorodiphenyl sulfone, a residence time of about 10 minutes generally is sufficient to provide a commercially acceptable conversion at elevated temperatures. A preferred retention time of about 15 to about 50 minutes yields about 15 to 50 percent sulfonic acid conversion.

The temperaturee at which the reactants contact is also not critical as long as it is above the minimum reaction temperature of about 180° C. However, to minimize the production of unwanted isomers and other by-products, moderate temperatures of from about 190° to about 240° C. are preferred.

The reaction between monochlorobenzene and chlorobenzene sulfonic acid to form 4,4'-dichlorodiphenyl sulfone is endothermic. Heating jackets and other conventional devices and methods may be employed to transfer heat to the reaction zone. A more convenient method is to supply heat with the vaporized monochlorobenzene or the chlorobenzene sulfonic acid. Therefore, it is preferred that the monochlorobenzene vapor be superheated to temperatures from about 220° to about 250° C. It is also preferred that the liquid chlorobenzene sulfonic acid be preheated to temperatures of from about 200° to about 220° C.

In the counter-current process, it is further preferred that monochlorobenzene be employed in excess so as to serve as entrainer to remove, from the reaction zone, the water generated in the reaction. As previously noted, the presence of water in the reaction zone greatly decreases the amount of 4,4'-dichlorodiphenyl sulfone formed. Generally, a 4 to 12 molar excess of monochlorobenzene is sufficient to efficiently remove the water from the reaction zone. A preferred amount of monochlorobenzene is from about 5 to about 8 moles per mole of chlorobenzene sulfonic acid in each reactor.

The excess monochlorobenzene, with entrained water, which exists as vapor from the reaction zone, will also generally contain minor amounts of chlorobenzene sulfonic acid and 4,4'-dichlorodiphenyl sulfone. As in conventional processes, the vapor may be condensed and the water removed by decanting or similar means to recover the monochlorobenzene which may then be recycled for further conversion.

However, to take further advantage of the improvement of this invention, the exit monochlorobenzene vapor is preferably employed further as entrainer in the dehydration of the recovered chlorobenzene sulfonic acid. Employment of the exit vapor in the dehydration step of this invention further enhances the process yield, as both the chlorobenzene sulfonic acid and diaryl sulfone present in the vapor are recovered during the dehydration.

Though the counter-current process of producing diaryl sulfone has been described in particular for the production of 4,4'-dichlorodiphenyl sulfone, the counter-current process is also applicable to the production of various other diaryl sulfones. The diaryl sulfone product formed in the process may be either a monosubstituted diaryl sulfone, polysubstituted diaryl sulfone or mixture thereof. Of course, the particular diaryl sulfone, or diaryl sulfones formed in the process is dependent on the monosubstituted benzene sulfonic acid and monosubstituted benzene reactants. Typical products of the process include, in addition to 4,4'-dichlorodiphenyl sulfone, ditolysulfone, difluorodiphenyl sulfone, and dibromodiphenyl sulfone, among others.

As the monosubstituted benzene reactant in the formation of diaryl sulfones, there may be employed any monosubstituted benzene having the formula:

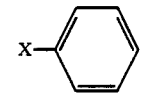

wherein X is hydrogen, halogen, a saturated alkyl radical having from 1 to 4 carbon atoms, or mixtures thereof. As benzene may be employed to form diaryl sulfones, and is encompassed by the above formula, it is to be understood that the use herein of the term "monosubstituted benzene" encompasses benzene. Examples of suitable monosubstituted benzene reactants include benzene, monochlorobenzene, monofluorobenzene, toluene, and monobromobenzene, among others.

The other reactant in the formation of diaryl sulfones is a monosubstituted benzene sulfonic acid having the formula:

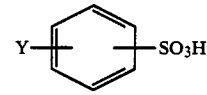

wherein Y is hydrogen, halogen, a saturated alkyl radical having from 1 to 4 carbon atoms, or mixtures thereof. The substituent Y on the benzene ring may be either ortho, meta, or para to the sulfonic acid substituent, though the more useful diaryl sulfones are generally those formed from para-substituted benzene sulfonic acids. Benzene sulfonic acid may be employed as a reactant and thus it is to be understood that the use herein of the term "monosubstituted benzene sulfonic acid" encompasses benzene sulfonic acid. Exemplary monosubstituted benzene sulfonic acids include benzene sulfonic acid, p-chlorobenzene sulfonic acid, p-bromobenzene sulfonic acid, toluene sulfonic acid, and p-fluorobenzene sulfonic acid, among others.

The monosubstituted benzene sulfonic acid reactant should be substantially anhydrous. Monosubstituted benzene sulfonic acids may be purchased or produced by any conventional process, such as those described in U.S. Patent Nos. 3,935,237 and 3,946,037. However, the recovery of the produced sulfonic acid in aqueous solutions containing large amounts of water, as is conventional and as taught by these references, is desirably not performed as the subsequent dehydration of the aqueous sulfonic acid is economically unattractive.

Instead it is preferred that the recovery and dehydration process steps constituting the improvement of this invention be employed in connection with the production of the monosubstituted benzene sulfonic acid to obtain anhydrous reactant.

A particularly convenient method of obtaining anhydrous sulfonic acid reactant is to add the sulfonic acid product mixture, prepared from a conventional synthesis process, to the reaction product mixture of the diaryl sulfone process and thereafter simultaneously recover and dehydrate the combined "new" and unreacted monosubstituted benzene sulfonic acid according to the process improvement of the present invention.

For instance, a particularly convenient and preferred method for producing chlorobenzene sulfonic acid reactant is by sulfonating monochlorobenzene with sulfur trioxide. The overall reaction may be represented by the following equation:

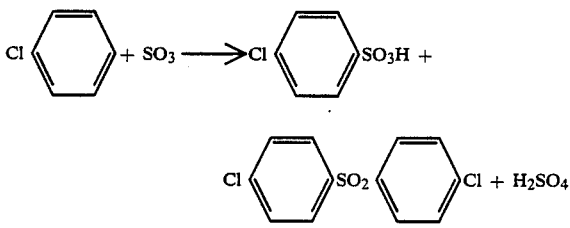

The reaction is rapid, exothermic, and essentially quantitative. About 80 mole percent of chlorobenzene sulfonic acid and about an equal molar amount of dichlorodiphenyl sulfone and sulfuric acid are formed. The chlorobenzene sulfonic acid is almost exclusively (generally >96%) the para isomer. The diaryl sulfone is an isomer mixture with about 96% 4,4'-dichlorodiphenyl sulfone.

In this formation of chlorobenzene sulfonic acid, it is preferred that monochlorobenzene be used in excess to serve as a reaction medium and as a solvent for the resulting chlorobenzene sulfonic acid. A preferred amount of monochlorobenzene is from about 2 to about 3 moles per mole of sulfur trioxide. Usually sulfur trioxide is employed in stabilized form such as the cyclic trimer form known as "Sulfan ®".

While the temperature of the sulfonation reaction is not critical, and may range from about −20° to about 230° C., it is preferable to maintain the reaction mixture at a moderate temperature, for example, from about 30° to 70° C. Moderate temperatures are desirable so that refrigeration will not be necessary prior to adding the p-chlorobenzene sulfonic acid solution to the diaryl sulfone reaction product mixture to achieve the phase separation. The temperature can be maintained by conventional means such as a heat exchanger or by controlling the rate at which sulfur trioxide is added to the monochlorobenzene.

In accordance with the improvement of the present invention, unreacted monosubstituted benzene sulfonic acid is recovered from a diaryl sulfone product mixture by an aqueous phase separation employing water in an amount less than the amount of the monosubstituted benzene sulfonic acid. Recovery is achieved in accordance with the finding that controlling the weight ratio of water to monosubstituted benzene sulfonic acid at less than 1:1 yields two phases whose specific gravities are sufficiently disparate that a heavier aqueous phase containing monosubstituted benzene sulfonic acid is readily separable from a lighter organic phase containing diaryl sulfone. The precise monosubstituted benzene sulfonic acid to water ratios that may be employed are, of course, dependent on the temperature at which the phase separation is conducted but are in general such that the specific gravity of the aqueous monosubstituted benzene sulfonic acid phase is appreciably greater than, preferably at least ten percent greater than, the specific gravity of the organic sulfone phase.

At a preferred separation temperature of about 70° to about 80° C., it has been found that a chlorobenzene sulfonic acid to water weight ratio between about 1:1 to about 4:1 yields an effective phase separation. At ratios significantly greater than 4:1 an effective phase separation is not obtained. At weight ratios less than 0.5:1, an effective phase separation is similarly not obtained and further increasing the amount of water results in phase inversion. As previously described, excessive amounts of water are undesirable as the water must later be removed from the chlorobenzene sulfonic acid prior to its use in producing sulfone. The preferred chlorobenzene sulfonic acid to water weight ratio is between about 2:1 to 3:1.

Though it is preferred that the aqueous phase separation proceed at temperatures between about 70° to 80° C. in the process improvement of this invention, the temperature may be anywhere between the freezing point to the boiling point of the separation solution. At both low and high temperatures effective phase separation, however, becomes increasingly more difficult and eventually becomes impractically inefficient.

To determine the amount of water that should be added, the chlorobenzene sulfonic acid content of the extraction mixture can be determined by titration of a sample with, for example, a solution of sodium hydroxide. The sulfuric acid is generally present in such a small amount that it can be ignored in making the determination. A more convenient method of determining the water to chlorobenzene sulfonic acid ratio is to monitor the conductivity of the aqueous mixture as water is added. Here again, because the sulfuric acid is present in such minor amount, it does not significantly interfere with the determination.

An organic solvent is used also in the improvement of this invention to effect the phase separation. The organic solvent dissolves the diaryl sulfone and forms the organic phase of the phase separation. Suitable organic solvents are those which dissolve the particular diaryl sulfone present but which are not appreciably water immiscible. Exemplary organic solvents include benzene, monochlorobenzene, toluene, mixtures thereof and the like. As unreacted monosubstituted benzene generally will be present in the diaryl sulfone reaction product mixture, its employment as the organic solvent is most convenient, e.g., chlorobenzene in the case of dichlorodiphenyl sulfone.

At least an amount of organic solvent sufficient to dissolve all the diaryl sulfone at the temperature of the separation is employed. Generally organic solvent in a weight amount of 2 to 3 times the amount of diaryl sulfone present is sufficient. Excessive amounts of organic solvent are not increasingly beneficial and may hamper the subsequent recovery of the diaryl sulfone.

After forming the aqueous phase separation, the lower aqueous monosubstituted benzene sulfonic acid layer is separated from the solution by conventional method, such as decanting, or similar means.

The remaining organic phase generally will still contain a minor portion of sulfonic acid. Prior to the recovery of diaryl sulfone, the crude product is usually neutralized. Thus, any sulfonic acid remaining is lost if no attempt is made to extract it from the organic sulfone product solution.

Accordingly, it is preferred to achieve as complete an extraction of monosubstituted benzene sulfonic acid from the crude product solution as is practical. Here, water is preferably added to the organic solution to effect a second phase separation. The amount of water in this secondary separation is not critical. If excess water is employed, phase inversion results with the dilute aqueous sulphonic acid phase rising to the top of the solution. The excess water is not here detrimental since it may be recycled and used in the formation of a subsequent initial phase separation. The amount of water employed, however, normally should not exceed that quantity desired for use in the initial aqueous phase separation of the sulfonic acid recovery. Of course, more limited amounts of water may be employed to effect a phase separation in the manner as in the initial sulfonic acid recovery and the resulting lower aqueous acid phase then may be recycled or passed to the dehydrator.

It is from the organic raffinate of this second separation that diaryl sulfone is recovered by suitable means such as crystallization, devolatization or similar means.

Similarly the aqueous sulfonic acid phase from the initial separation generally will still contain a minor amount of diaryl sulfone. Though the presence of sulfone in the sulfonic acid has no apparent detrimental effect on the dehydration and subsequent reaction of the sulfonic acid, the diaryl sulfone itself may possibly degrade during these process steps to yield undesirable isomeric sulfone compositions. Accordingly, it is generally desirable to reduce the diaryl sulfone content by a second phase separation prior to dehydrating and recycling the monosubstituted benzene sulfonic acid.

A second phase separation of the aqueous sulfonic acid is conveniently effected by adding organic solvent thereto. Here, the amount of organic solvent is not critical, though it must be sufficient to extract a major portion of the sulfone. However, excessive amounts of organic solvent bestow no additional benefit and may hamper the later recovery of the diaryl sulfone from the solvent. After the resulting organic sulfone phase is separated from the aqueous sulfonic acid, the diaryl sulfone may be recovered, or preferably, the entire solution may be recycled for use in a subsequent initial aqueous phase separation of a diaryl sulfone reaction product mixture.

The aqueous monosubstituted benzene sulfonic acid extract from the phase separation is dehydrated to recover monosubstituted benzene sulfonic acid which is sufficiently anhydrous to be employed as a reactant to form additional diaryl sulfone. As previously stated, syntheses of diaryl sulfone can generally tolerate the presence of water in amounts up to about one weight percent without significant detrimental consequences to product formation. Consequently, the monosubstituted benzene sulfonic acid is dehydrated to substantially anhydrous, and preferably to a water content of less than one weight percent.

Dehydration may be accomplished by any suitable means, though azeotropic distillation with entrainer is preferable. As entrainer, there may be employed organic liquids immiscible with water such as benzene, toluene, mixtures thereof and the like. An especially convenient entrainer is the monosubstituted benzene which is the coreactant in the diaryl sulfone synthesis, e.g., chlorobenzene in the case of dichlorodiphenyl sulfone. Employment of such material eliminates any need for removal of the entrainer from the monosubstituted benzene sulfonic acid prior to the recycle to form additional diaryl sulfone.

Dehydration of aqueous chlorobenzene sulfonic acid may be complicated due to the relatively high freezing points encountered during dehydration. Solutions of sulfonic acids with a high water content have freezing-points of from 0° to 30° C. However, at low water concentrations, monohydrates form which have appreciably higher freezing-points. At a water content of 8.5%, for example, aqueous chlorobenzene sulfonic acid has a freezing-point of about 101° C.

Accordingly, the formation of monohydrates during dehydration dictates the operating conditions of the dehydration, especially at the later stages as the sulfonic acid becomes more anhydrous. That is, by use of an entrainer or pressure, the boiling point of the aqueous sulfonic acid must be raised above its high freezing point.

However, elevated temperatures lead to hydrolysis of monosubstituted benzene sulfonic acid. Though the sulfuric acid resulting from hydrolysis will react to form again the sulfonic acid, the hydrolysis reaction is nonetheless highly undesirable as it is likely that the reformation will lead to enhanced amounts of undesirable isomers.

For example, the reformation of chlorobenzene sulfonic acid from sulfuric acid is not as isomer specific as the sulfonation of monochlorobenzene with sulfur trioxide and thus the hydrolysis leads to greater amounts of metachlorobenzene sulfonic acid. In addition, para-chlorobenzene sulfonic acid is more than 10 times as readily hydrolyzed as meta-chlorobenzene sulfonic acid. Thus, hydrolysis may change the sulfonic acid isomer ratio unfavorably and eventually result in enhanced formation of undesired diaryl sulfone isomers.

To minimize hydrolysis, the temperature of the dehydration should be kept as low as feasible, yet achieve appreciable dehydration rates. In the case of chlorobenzene sulfonic acid, the dehydration temperature is preferably from about 150° to about 180° C.

In order to conserve energy, the azeotropic dehydration may be achieved by using, as entrainer, the monosubstituted benzene vapor stream from the reactors when a counter-current diaryl sulfone process is employed. In addition to utilizing the heat content of this superheated stream, entrained acid and diaryl sulfone will be removed from the vapor stream during the dehydration. The entrainer from the dehydrator then can be reemployed as a reactant to form additional diaryl sulfone.

The anhydrous sulfonic acid, from the dehydration, is reacted with monosubstituted benzene reactant to obtain additional diaryl sulfone.

The following examples are provided to illustrate various aspects of the present invention. They are not intended to limit the scope of the invention, rather they are presented to facilitate the practice of the invention by those of ordinary skill in the art.

EXAMPLE 1

The following is an example of preparing chlorobenzene sulfonic acid. 300 pounds of monochlorobenzene was charged to a jacketed 50 gallon, glass-lined tank equipped with an external cooling loop. The tank was held at 70° C. with tempered water on the jacket. Then 100 pounds of sulfur trioxide was added over a 45 minute period. The excess monochlorobenzene served as solvent.

A typical product analysis was, on a weight basis:

| | |
|---|---|
| chlorobenzene sulfonic acid | 48.1% |
| sulfuric acid | 3.1% |
| dichlorodiphenyl sulfone | 9.0% |
| monochlorobenzene | 39.8% |

EXAMPLE 2

This example illustrates the counter-current reaction of monochlorobenzene with chlorobenzene sulfonic acid to form 4,4'-dichlorodiphenyl sulfone.

The reactor system consisted of two, four-inch by twelve-foot, packed columns connected in series. The packing was one-half inch ceramic Intalox saddles. The columns were traced and heated with circulating hot oil at the reaction temperature.

A chlorobenzene sulfonic acid (CBSA) feed stream was prepared as in Example 1 and preheated to 160° C. The feed entered at the top of the upper reactor and flowed from the upper reactor through a seal (pipe loop) to the top of the lower reactor.

Superheated monochlorobenzene (MCB) at 250° C. was individually metered to the bottom of each reactor. The monochlorobenzene vapor rose upwards in the reactors and exited at the top of each reactor.

The crude reaction product flowed from the bottom reactor into a tank.

The reactors were operated essentially adiabatically and used the superheated monochlorobenzene as heat source for the slightly endothermic reaction. As a result, in the top reactor the temperature was about 210° C. at the top, about 225° C. slightly above the middle of the column, and about 235° C. at the bottom. In the lower reactor, the temperature was 215° C. at its top and 237° C. at its bottom.

The process was conducted continuously over an eleven-day period. The feed rates and the product rate and composition from the reactors of the process are set forth in Table I. All percentages in this and the following Examples are by weight.

TABLE I

| | Feed Rate - LB/HR | | | | | PRODUCT RATE AND COMPOSITION | | | | | | |
|---|---|---|---|---|---|---|---|---|---|---|---|---|
| DAY | MCB | H₂O* | H₂SO₄* | CBSA | SUL-FONE* | TOTAL lb/hr | % MCB | % H₂O | % H₂SO₄ | % CBSA | % SUL-FONE | % 4,4** | % CON-VERSION*** |
| 1 | 0.6 | 0.9 | 0.9 | 22.5 | 0.3 | 28 | 5.4 | 0.1 | 1.4 | 62.8 | 30.3 | 88.8 | 23.0 |
| 2 | — | — | — | — | — | — | 8.8 | 0.2 | 1.4 | 64.0 | 25.6 | 89.0 | — |
| 3 | 1.4 | 0.8 | 1.0 | 22.7 | 0.2 | 28 | 10.0 | 0.1 | 1.4 | 62.5 | 26.0 | 89.5 | 20.7 |
| 4 | 1.4 | 0.7 | 0.8 | 20.8 | 0.2 | 23 | 7.9 | 0.1 | 1.4 | 64.4 | 26.2 | 89.2 | 20.2 |
| 5 | — | — | — | — | — | 26 | 4.8 | 0.1 | 1.5 | 65.8 | 27.8 | 89.5 | — |
| 6 | — | — | 1.0 | 21.6 | 0.2 | 29 | 9.5 | 0.1 | 1.4 | 66.1 | 22.9 | 88.6 | 17.8 |
| 7 | — | — | — | — | — | 28 | 6.3 | 0.1 | 1.3 | 62.2 | 30.1 | 88.1 | — |
| 8 | — | — | — | — | — | — | — | — | — | — | — | — | — |
| 9 | — | — | 1.1 | 25.3 | 0.1 | 29.7 | 8.6 | 0.1 | 1.3 | 63.7 | 26.3 | 88.0 | 20.8 |
| 10 | 2.0 | 0.9 | 1.0 | 26.0 | 0.2 | 32 | 10.6 | 0.1 | 1.4 | 63.0 | 24.9 | 87.7 | 19.9 |
| 11 | 1.7 | 0.9 | 0.9 | 22.4 | 0.2 | 24.2 | 8.4 | 0.1 | — | — | — | — | 19.9 |
| Avg. | 1.4 | 0.8 | 1.0 | 23.0 | 0.2 | 27.5 | 8.0 | 0.1 | 1.4 | 63.7 | 26.8 | 87.2 | 20.8 |

*Introduced as a component of the CBSA FEED
**The percentage of 4,4' dichlorodiphenyl sulfone produced is based on the total amount of sulfone produced.
***The percent conversion is based on the CBSA and sulfuric acid feed.

EXAMPLE 3

The aqueous phase separation of chlorobenzene sulfonic acid from 4,4'-dichlorodiphenyl sulfone is illustrated by this example. A chlorobenzene sulfonic acid make-up stream, prepared as in Example 1, was passed to a tank where it was mixed with diluent monochlorobenzene and the reactor product streams from Example 2.

A water-cooled heat exchanger system installed on the tank cooled and maintained the mixture at 70° C. The composition of this product mixture, which was the feed stream to the extractor, is set forth in Table II.

TABLE II

| | EXTRACTOR FEED COMPOSITION | | | | |
|---|---|---|---|---|---|
| DAY | % MCB | % H₂O | % H₂SO₄ | % CBSA | % SULFONE |
| 1 | 41.2 | 0.4 | 1.8 | 40.7 | 15.9 |
| 2 | 39.2 | 0.4 | 1.7 | 42.3 | 16.4 |
| 3 | 43.2 | 0.3 | 1.5 | 38.9 | 16.1 |
| 4 | 42.7 | 0.4 | 1.5 | 40.0 | 15.4 |
| 5 | — | — | — | — | — |
| 6 | — | — | — | — | — |
| 7 | — | — | — | — | — |
| 8 | 44.2 | 0.4 | 1.5 | 38.7 | 15.2 |
| 9 | 43.3 | 0.4 | 1.5 | 39.3 | 15.5 |
| 10 | 43.2 | 0.4 | 1.4 | 38.4 | 16.6 |
| 11 | 42.8 | 0.4 | 1.2 | 39.4 | 16.2 |
| AVG | 42.7 | 0.4 | 1.5 | 39.8 | 15.9 |

Thereafter, water was added in an amount to maintain a chlorobenzene sulfonic acid to water weight ratio of from 2.0 to 2.5 as determined by a titration with 1N NaOH solution (the small amount of H₂SO₄ was ignored). The mixture was then passed to a decanter. A second extraction was then performed to remove diaryl sulfone from the aqueous chlorobenzene sulfonic acid extract from the primary extraction. A four-inch RDC column with eight stages was used.

Monochlorobenzene was metered in the bottom of the extractor and represented the continuous phase. The aqueous chlorobenzene sulfonic acid was introduced at the top and dispersed by the rotors. The interface was controlled.

The composition of the resulting raffinate is set forth in Table III.

TABLE III

| | RAFFINATE COMPOSITION | | | |
|---|---|---|---|---|
| DAY | % CBSA | % H₂O | % MCB | % SULFONE |
| 1 | 55.6 | 34.7 | 7.0 | 0.6 |
| 2 | 55.7 | 34.5 | 6.7 | 0.6 |
| 3 | 54.8 | 34.5 | 8.5 | 0.3 |
| 4 | 54.6 | 36.6 | 6.1 | 0.7 |
| 5 | — | — | — | — |
| 6 | — | — | — | — |
| 7 | — | — | — | — |
| 8 | — | — | — | — |
| 9 | — | — | — | — |
| 10 | — | — | — | — |
| 11 | 53.8 | 36.1 | 7.9 | 0.3 |

A second extraction was also performed to extract chlorobenzene sulfonic acid and sulfuric acid from the monochlorobenzene-diaryl sulfone raffinate from the first extraction to ensure minimization of the loss of chlorobenzene sulfonic acid.

A four-inch RDC column with eight stages was employed. Water, the continuous phase, was added at the bottom and a level controller at the top controlled the water flow. A water overflow, above the standard level, was provided. The organic phase from the first extraction was fed by gravity to the top of the column and dispersed by the rotors.

Periodically, a product sample was taken and mixed with an equal volume of deionized water. The pH of the water layer was then measured to obtain an estimate of the chlorobenzene sulfonic acid content of the crude product solution. The pH of the water layer ranged from 2.5 to 3.5 indicating a chlorobenzene sulfonic acid content of 600 to 60 ppm in the product stream.

The results of this second extraction are set forth in Table IV.

TABLE IV

| DAY | TOTAL lb/hr | % MCB | % SULFONE | SULFONE lb/hr |
|---|---|---|---|---|
| 1 | — | — | — | — |
| 2 | 27.9 | 71.1 | 28.9 | 8.1 |
| 3 | 26.9 | 72.7 | 27.3 | 7.3 |
| 4 | 28.0 | 73.7 | 26.3 | 7.4 |
| 5 | — | — | — | — |
| 6 | — | — | — | — |
| 7 | — | — | — | — |
| 8 | 28.1 | 69.6 | 30.4 | 8.5 |
| 9 | 27.7 | 69.5 | 30.5 | 8.5 |
| 10 | 27.0 | 77.5 | 22.5 | 6.1 |
| 11 | 28.2 | 71.2 | 28.8 | 8.1 |
| AVG | 27.7 | 72.2 | 27.8 | 7.7 |

EXAMPLES 4–14

Extraction of chlorobenzene sulfonic acid from a 4,4'-dichlorodiphenyl sulfone mixture was also performed in the laboratory. Table V sets forth the results of these Examples.

TABLE V

| | LABORATORY EXTRACTIONS | | | | | | | | | | | | | | |
|---|---|---|---|---|---|---|---|---|---|---|---|---|---|---|---|
| | FEED COMPOSITION - GRAMS | | | | | | EXTRACT COMPOSITION | | | | | RAFFINATE COMPOSITION | | | |
| Example | TOTAL | H₂O | CBSA | MCB | SULFONE | H₂O/CBSA | TOTAL | H₂O | CBSA | MCB | SULFONE | TOTAL | H₂O | CBSA | MCB | SULFONE |
| 4 | 45.5 | 6.0 | 18.6 | 10.1 | 10.8 | 3.10 | 13.6 | — | 0.4 | 6.0 | 7.2 | 31.9 | 6.0 | 18.2 | 4.1 | 3.6 |
| 5 | 55.8 | 6.0 | 18.8 | 20.1 | 10.9 | 3.13 | 24.6 | — | 0.3 | 15.6 | 8.7 | 31.2 | 6.0 | 18.5 | 4.5 | 2.2 |
| 6 | 65.9 | 6.0 | 18.6 | 30.5 | 10.8 | 3.10 | 36.1 | — | 0.3 | 26.2 | 9.6 | 29.8 | 6.0 | 18.3 | 4.3 | 1.2 |
| 7 | 47.4 | 4.0 | 18.4 | 14.3 | 10.7 | 4.60 | 12.0 | — | 0.3 | 6.5 | 5.2 | 35.4 | 4.0 | 18.1 | 7.8 | 5.5 |
| 8 | 48.5 | 3.8 | 18.6 | 15.3 | 10.8 | 4.89 | 7.6 | — | 0.4 | 3.7 | 3.5 | 40.9 | 3.8 | 18.2 | 11.6 | 7.3 |
| 9 | 48.5 | 5.1 | 18.4 | 14.7 | 10.3 | 3.61 | 15.5 | — | 0.4 | 9.6 | 5.5 | 33.0 | 5.1 | 18.0 | 5.1 | 4.8 |
| 10 | 54.3 | 5.4 | 18.4 | 20.1 | 10.4 | 3.41 | 23.5 | — | 0.2 | 16.0 | 7.3 | 30.8 | 5.4 | 18.2 | 4.1 | 3.1 |
| 11 | 56.7 | 5.0 | 17.4 | 24.3 | 10.0 | 3.48 | 29.4 | — | 0.2 | 21.5 | 7.7 | 27.3 | 5.0 | 17.2 | 2.8 | 2.3 |
| 12 | 68.6 | 5.2 | 18.1 | 35.3 | 10.0 | 3.48 | 40.3 | — | 0.4 | 31.5 | 8.4 | 28.3 | 5.2 | 17.2 | 3.8 | 1.6 |
| 13 | 51.1 | 8.8 | 18.5 | 13.4 | 10.4 | 2.10 | 20.0 | — | 0.2 | 11.8 | 8.0 | 31.1 | 8.8 | 18.3 | 1.6 | 2.4 |
| 14 | 50.5 | 6.9 | 18.0 | 15.5 | 10.1 | 2.61 | 19.8 | — | 0.2 | 12.2 | 7.4 | 30.7 | 6.9 | 17.8 | 3.3 | 2.7 |

EXAMPLE 15

To illustrate the dehydration of aqueous chlorobenzene sulfonic acid, the extract from the second extraction of Example 3, as set forth in Table III, was dehydrated in a single stage dehydrator consisting of a 20 gallon, glass-lined tank, a circulating pump, a heat exchanger and a 6 inch Pyrex glass column. The column consisted of two 30 inch packed sections (one-half inch Intalox saddles) separated by a feed section.

On start-up, the dehydrator was charged with monochlorobenzene and heated to boiling. The aqueous chlorobenzene sulfonic acid extract and monochlorobenzene as entrainer were introduced at atmospheric pressure through the vapor line between the glass-lined vessel and the column. As water was removed and the concentration of the chlorobenzene sulfonic acid in the bottoms rose, the temperature increased. When the temperature reached 120° C., vacuum was slowly applied to achieve a pressure of 100 mm Hg. Once the vacuum was attained, the semibatch operation was continued until the temperature reached 150° C.

The dehydrator was then operated by feeding the aqueous chlorobenzene sulfonic acid extract (57% chlorobenzene sulfonic acid) at a rate of about 36 lb/hr, feeding the monochlorobenzene entrainer at about 90 lb/hr and feeding the monochlorobenzene reflux (to the top of the column) at about 5 lb/hr. Under these conditions, about 11 lbs of water were removed per hour and the monochlorobenzene overhead vapor was removed at about 145 lb/hr. About 25 lbs of 85% chlorobenzene sulfonic acid were produced per hour.

EXAMPLE 16

The process according to Example 15 was repeated except that a pre-dehydrator was installed before the dehydrator described in Example 15 to achieve a lower water content in the chlorobenzene sulfonic acid recycle feed to the reactors.

The pre-dehydrator was a 6 inch distillation column with two, 24 inch, packed sections separated by a feed section.

The pre-dehydrator was operated at atmospheric pressure. A bottoms temperature of 140° C. was employed to minimize hydrolysis. A side feed to the column was used to enhance dehydration in a stripping section. A chlorobenzene sulfonic acid extract was fed at a rate of about 35 lb/hr.

The monochlorobenzene entrainer flow rate was about 90 lb/hr which provided a monochlorobenzene-water composition with an atmospheric boiling point of 110° C. at the top of the column. This assured temperatures within the column above the freeze-point of the chlorobenzene sulfonic acid monohydrate. The monochlorobenzene reflux was fed to the top of the dehydrator at about 45 lb/hr.

The bottoms of the pre-dehydrator was fed to the middle of the column on the dehydrator of Example 15. The freeze-point of this material was lower than the hydrate (being sufficiently dehydrated) and above the melting point of the anhydrous chlorobenzene sulfonic acid (63° C.).

The bottoms temperature of the dehydrator was set at 180° and the pressure at 400 mm Hg. The monochlorobenzene entrainer flow rate was about 90 lb/hr and the reflux flow rate was about 45 lb/hr.

The pre-dehydrator reduced the water concentration of the feed from 25% to about 5%. The dehydrator lowered the water content further to less than 0.5%. The substantially anhydrous chlorobenzene sulfonic acid was produced at a rate of 25 lb/hr.

Based on the continuous eleven-day process operation of Examples 1, 2, 3, and 16, the efficiency of the process employing the improvements of this invention was calculated based on the amount of sulfur trioxide employed. As shown in Table VIII, an efficiency of 97.7% was obtained on an average over the 11-day operating perod. Furthermore, of the sulfone produced, 87–89% was 4,4′-dichlorodiphenyl sulfone.

TABLE VIII

| | PROCESS EFFICIENCY | | | | | |
|---|---|---|---|---|---|---|
| | SO$_3$ REACTANT FEED | | SULFONE PRODUCT | | | |
| DAY | lb/hr | m mole/hr | lb/hr | m mole/hr | % 4.4 | EFFICIENCY % |
| 1 | — | — | — | — | — | — |
| 2 | 2.32 | 29.03 | 8.10 | 28.1 | 89.3 | 96.7 |
| 3 | 1.97 | 24.59 | 7.34 | 25.59 | 89.4 | 104.1 |
| 4 | 2.30 | 28.74 | 7.36 | 25.66 | 88.7 | 89.3 |
| 5 | — | — | — | — | — | — |
| 6 | — | — | — | — | — | — |
| 7 | — | — | — | — | — | — |
| 8 | 2.20 | 27.55 | 8.54 | 29.76 | 88.8 | 108.0 |
| 9 | 2.30 | 28.74 | 8.45 | 29.44 | 88.7 | 102.4 |
| 10 | 1.87 | 23.40 | 6.08 | 21.17 | 87.2 | 90.5 |
| 11 | 2.44 | 30.51 | 8.12 | 28.30 | 87.3 | 92.8 |
| AVG | 2.20 | 27.50 | 7.71 | 26.86 | — | 97.7 |

EXAMPLE 17

This example illustrates the importance of using a weight ratio of monochlorobenzene sulfonic acid to water of from 4:1 to 1:1 in separating monochlorobenzene sulfonic acid from 4,4′-dichlorodiphenyl sulfone. A feed composition comprising 2.4% by weight sulfuric acid, 34.6% by weight chlorobenzene sulfonic acid, 22.5% by weight 4,4′-dichlorodiphenyl sulfone and 40.5% monochlorobenzene simulating the feed stock formed by combining chlorobenzene sulfonic acid make-up stream of Example 1, diluent monochlorobenzene and the reactor product stream of Example 2 as described in Example 3 was contacted with water at 70° C. or 80° C. as set forth in Table IX. The specific gravities of the aqueous and organic phases are also recorded in Table IX.

TABLE IX

| | SPECIFIC GRAVITIES OF PHASES | | | |
|---|---|---|---|---|
| CBSA/H$_2$O | 70° C. | | 80° C. | |
| Weight Ratio | Organic | Aqueous | Organic | Aqueous |
| No Water | 1.282 | | 1.272 | |
| 5:1 | 1.281 | | 1.267 | |
| 4:1 | 1.154 | 1.316 | 1.140 | 1.314 |
| 3:1 | 1.158 | 1.321 | 1.148 | 1.317 |
| 2.5:1 | 1.158 | 1.319 | 1.150 | 1.318 |
| 2:1 | 1.160 | 1.301 | 1.152 | 1.296 |
| 1:1 | 1.162 | 1.225 | 1.153 | 1.220 |
| 1:2* | 1.164 | 1.143 | 1.158 | 1.138 |

*Phase inversion occurred.

The above data clearly shows that a 4:1 to 1:1 weight ratio of chlorobenzene sulfonic acid to water is necessary in order to get a clean separation of the chlorobenzene sulfonic acid in the aqueous lower phase from the 4,4′-dichlorodiphenyl sulfone upper organic phase. When the chlorobenzene sulfonic acid to water weight ratio is above about 4:1 (e.g. 5:1) there is no phase separation. When the chlorobenzene sulfonic acid to water weight ratio is below 1:1 (e.g. 1:2) the organic phase is heavier than the aqueous phase and the product 4,4′-dichlorodiphenyl sulfone is in the lower phase.

We claim:

1. A process for preparing 4,4′-dichlorodiphenyl sulfone comprising contacting monochlorobenzene with p-chlorobenzene sulfonic acid thereby forming a reaction product mixture comprising at least one diaryl sulfone and unreacted chlorobenzene sulfonic acid, the improvement comprising the steps of:
    (a) adding water in an amount such that the weight ratio of chlorobenzene sulfonic acid to water is between about 1:1 to 4:1 to the reaction product mixture thereby forming in the reaction product mixture a heavier aqueous phase containing unreacted monochlorobenzene sulfonic acid and a lighter organic phase containing 4,4′-dichlorodiphenyl sulfone;

(b) separating the aqueous phase from the lighter organic phase;

(c) dehydrating the aqueous phase thereby recovering unreacted substantially anhydrous chlorobenzene sulfonic acid; and (d) contacting the recovered unreacted chlorobenzene sulfonic acid with monochlorobenzene thereby forming additional 4,4'-dichlorodiphenyl sulfone.

2. The process of claim 1 wherein the ratio of chlorobenzene sulfonic acid to water is between about 2:1 to 3:1.

3. A process for preparing 4,4'-dichlorodiphenyl sulfone comprising:

(a) passing liquid p-chlorobenzene sulfonic acid into a reaction zone while passing monochlorobenzene vapor into the reaction zone counter-current to the p-chlorobenzene sulfonic acid thereby forming 4,4'-dichlorodiphenyl sulfone;

(b) removing unreacted p-chlorobenzene sulfonic acid with 4,4'-dichlorodiphenyl sulfone from the reaction zone as a reaction product mixture;

(c) adding water to the reaction product mixture in an amount such that the weight ratio of chlorobenzene sulfonic acid to water is between about 1:1 to 4:1 thereby forming in the reaction product mixture a heavier aqueous phase containing unreacted p-chlorobenzene sulfonic acid and a lighter organic phase containing 4,4'-dichlorodiphenyl sulfone;

(d) separating the aqueous phase from the lighter organic phase;

(e) dehydrating the aqueous phase thereby recovering unreacted p-chlorobenzene sulfonic acid;

(f) repeating step (a) with the recovered p-chlorobenzene sulfonic acid; and (g) recovering 4,4'-dichlorodiphenyl sulfone.

4. The process of claim 3 wherein the ratio of chlorobenzene sulfonic acid to water is between about 2:1 to 3:1.

5. A process for preparing 4,4'-dichlorodiphenyl sulfone comprising:

(a) reacting sulfonating agent comprising sulfur trioxide with an excess of monochlorobenzene thereby forming a product mixture containing predominately p-chlorobenzene sulfonic acid with monochlorobenzene entrainer;

(b) passing a portion of the p-chlorobenzene sulfonic acid product mixture into a reaction zone while passing monochlorobenzene vapor counter-current to the p-chlorobenzene sulfonic acid thereby forming predominately 4,4'-dichlorodiphenyl sulfone;

(c) recovering unreacted monochloro benzene vapor from the reaction zone;

(d) removing unreacted p-chlorobenzene sulfonic acid with 4,4'-dichlorodiphenyl sulfone from the reaction zone as a reaction product mixture;

(e) adding (i) a portion of the p-chlorobenzene sulfonic acid mixture and (ii) water to the reaction product mixture in an amount such that the weight ratio of chlorobenzene sulfonic acid to water is between about 1:1 to 4:1 thereby forming in the reaction product mixture a heavier aqueous phase containing p-chlorobenzene sulfonic acid and a lighter organic phase containing 4,4'-dichlorodiphenyl sulfone with a monochlorobenzene;

(f) separating the aqueous phase from the lighter organic phase;

(g) recovering the 4,4'-dichlorodiphenyl sulfone from the organic phase;

(h) dehydrating the aqueous phase by azeotropic distillation with the recovered monochlorobenzene vapor as entrainer, thereby recovering unreacted substantially anhydrous p-chlorobenzene sulfonic acid; and (i) passing the recovered unreacted p-chlorobenzene sulfonic acid into a reaction zone while passing monochlorobenzene countercurrent to the p-chlorobenzene sulfonic acid thereby forming additional 4,4'-dichlorodiphenyl sulfone.

6. The process of claim 5 wherein step (e) includes adding liquid monochlorobenzene to the reaction product mixture in an amount such that the 4,4'-dichlorodiphenyl sulfone is dissolved in monochlorobenzene.

7. A process for preparing 4,4'-dichlorodiphenyl sulfone which comprises the steps of:

(a) reacting liquid p-chlorobenzene sulfonic acid in a reaction zone with monochlorobenzene thereby forming 4,4'-dichlorodiphenyl sulfone;

(b) removing unreacted p-chlorobenzene sulfonic acid with 4,4'-dichlorodiphenyl sulfone from the reaction zone as a reaction product mixture;

(c) reacting a sulfonating agent comprising sulfur trioxide with an excess of monochlorobenzene thereby forming predominately p-chlorobenzene sulfonic acid product mixture with monochlorobenzene entrainer;

(d) combining 4,4'-dichlorodiphenyl sulfone formed in step (b) and p-chlorobenzene sulfonic acid product mixture formed in step (c);

(e) forming an aqueous composition comprising the composition of step (d) wherein the weight ratio of chlorobenzene sulfonic acid to water in the composition is about 1:1 to 4:1 thereby forming a heavier aqueous phase containing p-chlorobenzene sulfonic acid and a lighter organic phase containing 4,4'-dichlorodiphenyl sulfone;

(f) separating the aqueous phase friom the lighterr organic phase;

(g) dehydrating the aqueous phase thereby recovering unreacted substantially anhydrous chlorobenzene sulfonic acid; and (h) contacting the recovered unreacted chlorobenzene sulfonic acid with monochlorobenzene thereby forming additional 4,4'-dichlorodiphenyl sulfone.

8. The process of claim 7, wherein in step (a) liquid p-chlorobenzene sulfonic acid and monochlorobenzene vapor are passed countercurrent in the reaction zone.

9. The process of claim 7 wherein the water in step (e) is added to the composition of step (d).

* * * * *